United States Patent
Rose

(10) Patent No.: US 11,897,202 B2
(45) Date of Patent: *Feb. 13, 2024

(54) METHOD FOR 3D PRINTING

(71) Applicant: Daniel Todd Rose, Wilmington, NC (US)

(72) Inventor: Daniel Todd Rose, Wilmington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,794

(22) Filed: Apr. 10, 2023

(65) Prior Publication Data

US 2023/0321913 A1    Oct. 12, 2023

Related U.S. Application Data

(60) Provisional application No. 63/362,785, filed on Apr. 11, 2022.

(51) Int. Cl.
*B29C 44/02* (2006.01)
*B29C 64/112* (2017.01)
(Continued)

(52) U.S. Cl.
CPC ............ *B29C 64/386* (2017.08); *A61B 34/20* (2016.02); *A61L 27/18* (2013.01); *A61L 27/54* (2013.01);
(Continued)

(58) Field of Classification Search
CPC ......... A27L 27/54; A27L 27/56; B29C 44/02; B29C 44/022; B29C 44/3415;
(Continued)

(56) References Cited

U.S. PATENT DOCUMENTS

| | | | | |
|---|---|---|---|---|
| 2002/0059049 A1* | 5/2002 | Bradbury | ........... | G05B 19/4099 264/308 X |
| 2003/0180344 A1* | 9/2003 | Wise | ....................... | A61L 27/56 424/423 |

(Continued)

FOREIGN PATENT DOCUMENTS

| | | | | |
|---|---|---|---|---|
| CN | 112184909 | | 1/2021 | |
| WO | WO-2020142888 A1 * | | 7/2020 | ............. B33Y 70/00 |

OTHER PUBLICATIONS

International Search Report, dated Aug. 18, 2023, from corresponding International Application No. PCT/US2023/018073.
(Continued)

*Primary Examiner* — Leo B Tentoni
(74) *Attorney, Agent, or Firm* — Brient IP Law, LLC

(57) ABSTRACT

A method for 3D printing a patient-specific bone implant having variable density, in various aspects, comprises: (1) providing a thermoplastic polymer composition comprising: (A) between about 20% and about 50% bioactive agent by weight; (B) between about 0.5% and about 10% chemical foaming agent by weight; and (C) balance structural polymer by weight; (2) receiving, by computing hardware, a scan of a bone, the scan comprising at least a 3D image of the bone and radiodensity data for the bone; and (3) causing, by the computing hardware, a 3D printer to form the patient-specific bone implant from the 3D image using the thermoplastic polymer by modifying a 3D printing temperature of the 3D printer during printing of the patient-specific bone implant such that each portion of the patient-specific bone implant is produced at a temperature that corresponds to a desired density defined by the radiodensity data for the bone.

20 Claims, 8 Drawing Sheets

(51) Int. Cl.

| | |
|---|---|
| *B29C 64/118* | (2017.01) |
| *B29C 64/124* | (2017.01) |
| *B29C 64/153* | (2017.01) |
| *B29C 64/165* | (2017.01) |
| *B33Y 10/00* | (2015.01) |
| *G01N 23/046* | (2018.01) |
| *G05B 19/4099* | (2006.01) |
| *B29C 64/386* | (2017.01) |
| *A61L 27/54* | (2006.01) |
| *A61L 27/18* | (2006.01) |
| *A61L 27/56* | (2006.01) |
| *B33Y 70/00* | (2020.01) |
| *B33Y 80/00* | (2015.01) |
| *B33Y 50/00* | (2015.01) |
| *A61B 34/20* | (2016.01) |
| *B29C 44/34* | (2006.01) |
| *B29L 31/00* | (2006.01) |
| *A61B 34/10* | (2016.01) |
| *B29K 67/00* | (2006.01) |
| *B29K 105/04* | (2006.01) |
| *B29K 33/00* | (2006.01) |
| *B29K 71/00* | (2006.01) |

(52) U.S. Cl.
CPC ............ *A61L 27/56* (2013.01); *B29C 44/022* (2013.01); *B29C 44/3415* (2013.01); *B33Y 50/00* (2014.12); *B33Y 70/00* (2014.12); *B33Y 80/00* (2014.12); *A61B 2034/105* (2016.02); *A61B 2034/108* (2016.02); *A61L 2300/112* (2013.01); *A61L 2430/02* (2013.01); *B29K 2033/12* (2013.01); *B29K 2067/043* (2013.01); *B29K 2067/046* (2013.01); *B29K 2071/00* (2013.01); *B29K 2105/04* (2013.01); *B29L 2031/7532* (2013.01); *G05B 2219/49013* (2013.01); *G05B 2219/49016* (2013.01); *G05B 2219/49018* (2013.01); *G05B 2219/49021* (2013.01); *G05B 2219/49023* (2013.01); *G05B 2219/49026* (2013.01); *G06T 2207/10081* (2013.01); *G06T 2207/10116* (2013.01)

(58) Field of Classification Search
CPC ..... B29C 44/60; B29C 64/112; B29C 64/118; B29C 64/124; B29C 64/153; B29C 64/165; B29C 64/386; B29K 2033/12; B29K 2067/043; B29K 2067/046; B29K 2071/00; B29L 2031/7532; B33Y 10/00; B33Y 50/00; G01N 23/046; G05B 19/4099; G05B 2219/49013; G05B 2219/49016; G05B 2219/49018; G05B 2219/49021; G05B 2219/49023; G06T 2207/10081; G06T 2207/10116
USPC ....... 264/40.6, 54, 113, 308, 331.11, 331.21, 264/401, 497; 382/131, 132; 700/119, 700/120
See application file for complete search history.

(56) References Cited

U.S. PATENT DOCUMENTS

| | | | |
|---|---|---|---|
| 2016/0318247 A1* | 11/2016 | Schlachter | ............ B29C 64/118 |
| 2020/0009297 A1* | 1/2020 | Reinauer | ................ B33Y 70/00 |
| 2021/0186702 A1 | 6/2021 | Sariibrahimoglu et al. | |
| 2022/0154018 A1* | 5/2022 | Wang | ...................... A61L 27/56 |

OTHER PUBLICATIONS

Sutradhar, et al, "Designing Patient-Specific 3D Printed Craniofacial Implants Using a Novel Topology Optimization Method," Medical and Biological Engineering and Computing, Springer, Heildelberg, DE, vol. 54, No. 7, Dec. 11, 2015, pp. 1123-1135 (Year: 2015).
Temple, et al, "Engineering Anatomically Shaped Vascularized Bone Grafts with hASCs and 3D-Printed PCL Scaffolds," published online Feb. 19, 2014 in Wiley Online Library (wileyonlinelibrary. com); Journal of Biomedical Materials Research A, Dec. 2014, vol. 102A, Issue 12, pp. 4317-4325 (Year: 2014).
Written Opinion of the International Searching Authority, dated Aug. 18, 2023, from corresponding International Application No. PCT/US2023/018073.

* cited by examiner

METHOD FOR 3D PRINTING

CROSS-REFERENCE TO RELATED APPLICATIONS

This application claims the benefit of U.S. Provisional Patent Application Ser. No. 63/362,785, filed Apr. 11, 2022, the entire disclosure of which is hereby incorporated herein by reference in its entirety.

TECHNICAL FIELD

The present disclosure is generally related to foamable thermoplastic compositions for use in 3D printing applications.

BACKGROUND

Trauma that results in the loss of bone segments may require the use of three dimensional structure(s) to assist in bone regeneration (e.g., to provide a structure to which bone tissue and other cells can attach). Such structures may require various material properties throughout and customization in terms of size, surface texture, and other characteristics depending on a patient's particular injury. Accordingly, there is a need for improved systems and methods for producing bone implants.

SUMMARY

A method for 3D printing a patient-specific bone implant having variable density, in various aspects, comprises: (1) providing a thermoplastic polymer composition comprising: (A) between about 20% and about 50% bioactive agent by weight; (B) between about 0.5% and about 10% chemical foaming agent by weight; and (C) balance structural polymer by weight; (2) receiving, by computing hardware, a scan of a bone, the scan comprising at least a 3D image of the bone and radiodensity data for the bone; and (3) causing, by the computing hardware, a 3D printer to form the patient-specific bone implant from the 3D image using the thermoplastic polymer by modifying a 3D printing temperature of the 3D printer during printing of the patient-specific bone implant such that each portion of the patient-specific bone implant is produced at a temperature that corresponds to a desired density defined by the radiodensity data for the bone. In various aspects, the structural polymer comprises at least one of: (1) poly(lactic-acid); (2) poly(L-lactic acid); (3) poly(D-lactic acid); (4) poly(D-L-lactic acid); (5) poly-ether-ether-keytone; (6) poly-methyl methacrylate; or (7) poly(lactic-co-glycolic acid). In a particular aspect, the structural polymer comprises polylactic-acid (PLA). In some aspects, the bioactive agent comprises at least one of hydroxyapatite, calcium carbonate, bioactive glass, allograft bone components, silica nitrite, or tricalcium phosphate. In some aspects, the chemical foaming comprises citric acid.

In some aspects, the 3D printer comprises a heating element and a cooling element. In such aspects, causing the 3D printer to form the patient-specific bone implant from the 3D image using the thermoplastic polymer by modifying the printing temperature of the 3D printer during printing such that each portion of the patient-specific bone implant is produced at the temperature that corresponds to the desired density defined by the radiodensity data for the bone comprises causing each of the cooling element and the heating element to cooperate to heat the thermoplastic polymer composition to the temperature that corresponds to the desired density defined by the radiodensity data during 3D printing of each portion of the patient-specific bone implant. In some aspects, the method comprises determining, by the computing hardware, a 3D printing temperature for each portion of the patient-specific bone implant based on the radiodensity data and one or more properties of the thermoplastic polymer composition;

A method for producing a variable density 3D printed component, according to some aspects, comprises: (1) providing a thermoplastic polymer composition comprising: (A) between about 20% and about 50% bioactive agent by weight; (B) between about 0% and about 10% chemical foaming agent by weight; and (C) between about 40% and about 80% thermoplastic by weight; and (2) causing, by computing hardware, a 3D printer to form the variable density 3D printed component from a 3D model using the thermoplastic polymer composition by adjusting a 3D printing temperature of the 3D printer during printing of the variable density 3D printed component such that each portion of the variable density 3D printed component is produced at a temperature that corresponds to a desired density of each portion of the variable density 3D printed component. In some aspects, the thermoplastic comprises at least one of: (1) poly(lactic-acid); (2) poly(L-lactic acid); (3) poly(D-lactic acid); (4) poly(D-L-lactic acid); (5) poly-ether-ether-keytone; (6) poly-methyl methacrylate; or (7) poly(lactic-co-glycolic acid). In a particular embodiment, the thermoplastic comprises polylactic-acid (PLA).

In some aspects, the bioactive agent comprises hydroxyapatite. In various aspects, the chemical foaming comprises sodium bicarbonate, citric acid, or azodicarbonamide. In some aspects, the 3D printer comprises a heating element and a cooling element and causing the 3D printer to form the variable density 3D printed component comprises causing each of the cooling element and the heating element to cooperate to heat the thermoplastic polymer composition to the temperature that corresponds to the desired density. In some aspects, the method further comprises determining, by the computing hardware, the 3D printing temperature for each portion of the 3D printed component based on radiodensity data for the 3D printed component and one or more properties of the thermoplastic polymer composition. In various aspects, the method further comprises using imaging data and radiodensity data for a desired component to determine the 3D printing temperature for each portion of the 3D printed component. In some aspects, the method further comprising selecting the thermoplastic polymer composition such that the portion of bioactive agent, chemical foaming agent, and thermoplastic produces the desired density at the 3D printing temperature that corresponds to the desired density.

In particular aspects, the imaging data for the desired component comprises data derived from a CT scan. In some aspects, the desired component comprises a patient's bone, and the 3D printed component comprises a patient-specific bone implant that corresponds to the patient's bone. In some aspects, causing the 3D printer to form the variable density 3D printed component comprises causing the 3D printer to print each layer of the 3D printed component such that each portion of each layer is printed at a temperature that corresponds to the desired density. In various aspects, the method further comprises determining the temperature that corresponds to the desired density of each portion of the variable density 3D printed component based on radiodensity data for the 3D printed component and one or more properties of the thermoplastic polymer.

A method for producing a variable density 3D printed component, in some aspects, comprises: (1) providing a thermoplastic polymer composition comprising: (A) about 20% bioactive agent by weight; (B) between about 0.5% and about 1.5% chemical foaming agent by weight; and (C) between about 0% and about 79.5% thermoplastic by weight; and (2) causing, by computing hardware, a 3D printer to form the variable density 3D printed component from a 3D model using the thermoplastic polymer composition by adjusting a 3D printing temperature of the 3D printer during printing of the variable density 3D printed component such that each portion of the variable density 3D printed component is produced at a temperature that corresponds to a desired density of each portion of the variable density 3D printed component.

In some aspects, the thermoplastic comprises at least one of: (1) poly(lactic-acid); (2) poly(L-lactic acid); (3) poly(D-lactic acid); (4) poly(D-L-lactic acid); (5) poly-ether-ether-keytone; (6) poly-methyl methacrylate; or (7) poly(lactic-co-glycolic acid). In a particular aspects, the thermoplastic comprises polylactic-acid (PLA). In various aspects, the bioactive agent comprises hydroxyapatite. In a particular embodiment, the thermoplastic polymer composition comprises: (1) about 20% bioactive agent by weight; (2) about 0.5% chemical foaming agent by weight; and (3) about 79.5% thermoplastic by weight. In particular aspects, the thermoplastic polymer composition has a density following 3D printing at about 200 degrees Celsius of between about 1.21 g/cm^3 and about 1.29 g/cm^3. In a particular aspect, the thermoplastic polymer composition comprises: (1) about 20% bioactive agent by weight; (2) about 1.5% chemical foaming agent by weight; and (3) about 78.5% thermoplastic by weight. In some aspects, the thermoplastic polymer composition has a density following 3D printing at about 190 degrees Celsius of about 1.26 g/cm^3. In various aspects, the thermoplastic polymer composition has a density following 3D printing at about 200 degrees Celsius of between about 1.05 g/cm^3 and about 1.10 g/cm^3. In a particular aspect, the chemical foaming agent comprises citric acid.

A method for 3D printing a patient-specific bone implant having variable density, in some aspects, comprises: (1) providing a thermoplastic polymer composition comprising: (A) about 20% bioactive agent by weight; (B) between about 0.5% and about 1.5% chemical foaming agent by weight; and (C) balance structural polymer by weight; (2) receiving, by computing hardware, a scan of a bone, the scan comprising at least a 3D image of the bone and radiodensity data for the bone; and (3) causing, by the computing hardware, a 3D printer to form the patient-specific bone implant from the 3D image using the thermoplastic polymer by modifying a 3D printing temperature of the 3D printer during printing of the patient-specific bone implant such that each portion of the patient-specific bone implant is produced at a temperature that corresponds to a desired density defined by the radiodensity data for the bone.

In some aspects, the chemical foaming agent comprises citric acid. In particular aspects, the bioactive agent comprises hydroxyapatite. In some aspects, the structural polymer comprises polylactic acid. In particular aspects, the structural polymer comprises: (1) about 20% bioactive agent by weight; (2) about 1% chemical foaming agent by weight; and (3) about 79% thermoplastic by weight. In other embodiments, the structural polymer comprises: (1) about 20% bioactive agent by weight; (2) about 0.5% chemical foaming agent by weight; and (3) about 79.5% thermoplastic by weight. In some aspects, the structural polymer has a modulus of elasticity following 3D printing at about 200 degrees Celsius of between about 570 MPa and about 725 MPa. In various aspects, the structural polymer comprises: (1) about 20% bioactive agent by weight; (2) about 1.5% chemical foaming agent by weight; and (3) about 78.5% thermoplastic by weight. In such aspects, the structural polymer has a modulus of elasticity following 3D printing at about 200 degrees Celsius of between about 390 MPa and about 550 MPa. In some embodiments, the 3D printer comprises a heating element and a cooling element and causing the 3D printer to form the patient-specific bone implant from the 3D image using the thermoplastic polymer by modifying the printing temperature of the 3D printer during printing such that each portion of the patient-specific bone implant is produced at the temperature that corresponds to the desired density defined by the radiodensity data for the bone comprises causing each of the cooling element and the heating element to cooperate to heat the thermoplastic polymer composition to the temperature that corresponds to the desired density defined by the radiodensity data during 3D printing of each portion of the patient-specific bone implant.

BRIEF DESCRIPTION OF THE DRAWINGS

In the course of this description, reference will be made to the accompanying drawings, which are not necessarily drawn to scale, and wherein.

DETAILED DESCRIPTION

Figure 1:
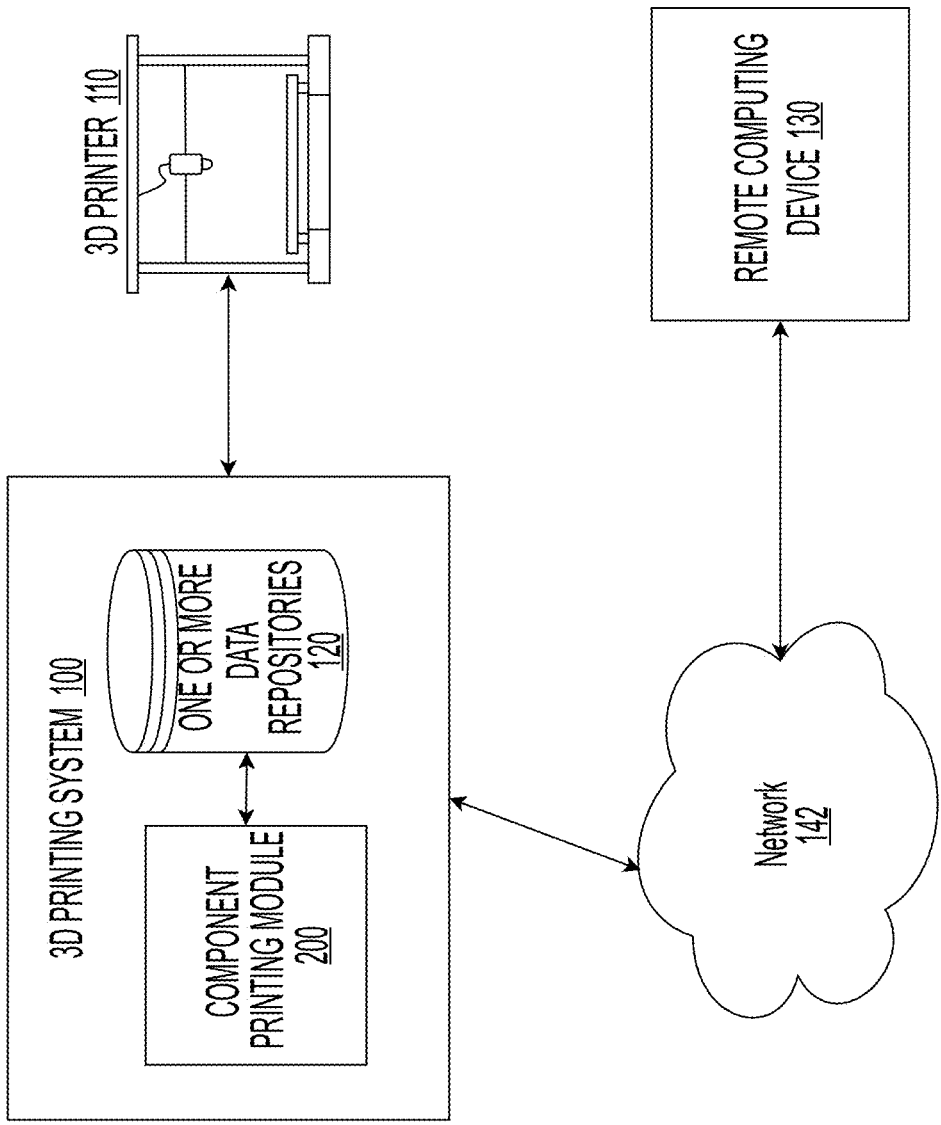
FIG. 1 depicts an example of a computing environment that can be used for generating a 3D printed component (e.g., such as a bone implant) in accordance with various embodiments of the present disclosure.

Various embodiments now will be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

Current orthopedic implants (e.g., bone implants) may be limited in the level of patient specificity and biological interaction they can achieve. For example, conventional metal implants may result in problems such as stress shielding, bone resorption, and poor osseointegration caused by a mismatch of modulus of elasticity between the metal implant and surrounding bone tissue. Current metal and thermoplastic implants are non-biodegradable, resulting in permanent implant fixtures. In the case of permanent implant fixtures, it may be necessary to perform a subsequent surgical procedure to remove the implant. Alternatively, non-biodegradable components may require a structural design that is intended to remain as a structural component of a replaced bone for the remainder of a patient's life.

Biodegradable thermoplastics (e.g., polylactic-acid) may be useful in orthopedic implants, as such materials may naturally dissolve (e.g., be absorbed by the body) after a particular period of time. As such, orthopedic implants made from biodegradable materials may allow bone growth and replacement prior to simply being resorbed by the patient's body. Such material selection may preclude the need for subsequent surgical procedures (i.e., to remove the implant) without needing to design the implant to remain permanently within the patient (i.e., because the implant will resorb after a certain period of time).

Designing implants from polymers and thermoplastics with mechanical properties that adhere as closely to the natural properties of bones as possible may reduce negative impacts on surrounding bone tissue. Doing so may be technically challenging, however, as the modulus of elasticity of bone may be patient-specific (e.g., the modulus of elasticity of bone varies from patient to patient as well as across different bones and/or portions of bone in a patient's body). Bone density can vary based on the type of bone, location in the body, as well as a patient's age and osteoporotic bone structures. Modulus of elasticity may also depend on a patient's specific bone density. As such, the efficacy of on orthopedic implant may be improved by the ability to produce orthopedic implants of varying density and modulus of elasticity, while reducing the potential negative impact to surrounding tissues.

Plastics that have mechanical properties that mirror those of bone may, however, not chemically interact with the body. Biologically inert materials may result in poor binding of bone. As such, it may be desirable to modify and/or supplement plastics used for orthopedic implants with additional material (e.g., via a coating or one or more additives) in order to enhance osteoblastic cell adhesion, growth, and differentiation. For example, in particular aspects, a bioactive agent may be added to a composition used as an orthopedic implant. In a particular embodiment, hydroxyapatite (HA) may be added to a thermoplastic composition to improve biological interaction between the implant and surrounding tissue. In some aspects, hydroxyapatite may further affect the modulus of elasticity of the implant as well as degradation behavior. In this way, a proportion of hydroxyapatite in a composite material may be tuned based on the desired properties of the implant produced from a particular composition.

In addition to various material issues and limitations discussed above, current implants may lack patient specificity. For example, implants constructed (e.g., mass-produced) from the same materials and molds (e.g., via injection molding) may lack the specificity required to replicate a particular patient's bone loss. In various aspects, 3D printing may provide greater flexibility with respect to producing patient specific implants in terms of size and shape. In particular, 3D printed implants may be produced from computer models of the desired implant. Currently, most 3D printed bone implants are manufactured using a titanium sintering process, that can be expensive and time-intensive. Various aspects may utilize Fused-Deposition-Modeling (FDM) 3D printing (e.g., Fused Filament Fabrication), which can further improve on the limitations of current 3D printing techniques and injection molding solutions for producing implants. FDM 3D printing may require relatively lower cost equipment and enable implant production on-site at hospitals.

FDM 3D printing may also improve specificity in replicating a patient's bone over conventional methods of implant manufacturing such as injection molding, because injection molding is not able to produce implants with varied material properties such as density, surface structure, and modulus of elasticity on a region-by-region basis throughout the implant. By integrating a temperature sensitive agent into the composition use to produce a 3D printed implant as discussed herein, the process described herein can produce a 3D printed implant whose properties (e.g., density, surface structure, and modulus of elasticity) vary in different portions of the implant.

By producing implants of varying density that more closely mirror the density and structure of a patient's specific bone for which an implant is being produced, the process described herein can manufacture implants that have improved interaction and regeneration of a patient's bone with the implant. Various embodiments of a foamable thermoplastic composition are described herein. As discussed more fully below, these foamable thermoplastic compositions may be utilized in a process for 3D printing patient-specific bone implants (and other components of varying density).

Foamable Thermoplastic Composition

A foamable thermoplastic composition, according to various embodiments described herein, is configured to 3D print a patient-specific orthopedic implant (e.g., bone implant) or other component. In particular embodiments, the foamable thermoplastic composition is configured for forming a 3D printed component (e.g., bone implant) having a density in each portion of the 3D printed component that corresponds to a temperature at which that portion of the 3D printed component was 3D printed. In some aspects, the foamable thermoplastic composition includes any suitable heat activated foaming agent operative to manufacture a bone growth substrate with a textured surface having pores on a macro level, a micro level, and/or a nanoparticle level to facilitate rapid bone growth. In other embodiments, the foamable thermoplastic composition includes any suitable chemical foaming agent that does not produce porosity or other texture.

According to some aspects, a foamable thermoplastic composition comprises: (1) a structural polymer (e.g., a biodegradable and/or non-biodegradable structural polymer; (2) a bioactive agent; and (3) a chemical foaming agent. In various embodiments, the structural polymer (e.g., a biodegradable and/or non-biodegradable structural polymer comprises any suitable bioabsorbable thermoplastic for providing structure to the 3D printed component (e.g., implant), while acting as a substrate for bone growth once the implant is surgically inserted into a patient. In various embodiments, the structural polymer may include, for example: (1) poly (lactic-acid); (2) poly(L-lactic acid); (3) poly(D-lactic acid); (4) poly(D-L-lactic acid); (5) poly-ether-ether-keytone; (6) poly-methyl methacrylate; (7) poly(lactic-co-glycolic acid); and/or (8) any other suitable biodegradable structural polymer or combination thereof. In any embodiment described herein, reference may be made to a particular embodiment comprising a biodegradable structural polymer. It should be understood in light of this disclosure that such embodiments may further include non-biodegradable structural polymer, entirely non-bridgeable structural polymer, or any other suitable structural polymer or combination of structural polymers (e.g., including a combination of multiple structural polymers that include both biodegradable and/or non-biodegradable polymers).

In particular embodiments, the bioactive agent may include hydroxyapatite powder. As discussed above, the hydroxyapatite powder (e.g., or other suitable bioactive agent) may be configured to improve biological interactions with surrounding tissue for orthopedic implants produced using the foamable thermoplastic composition. When used as a coating, hydroxyapatite powder and other bioactive agents may enhance osteoblastic cell adhesion, growth and differentiation. By integrating the hydroxyapatite powder or other bioactive agent into the foamable thermoplastic composition, orthopedic implants produced using various embodiments of the foamable thermoplastic composition may have improved osteoblastic cell adhesion, growth and differentiation (e.g., and therefore improved interaction with surrounding tissue) that implants produced using a thermoplastics that do not include a bioactive agent (e.g., that are not impregnated with or otherwise enhanced with the bioactive agent). In other embodiments, the bioactive agent (e.g., hydroxyapatite) may further be used as a coating for the orthopedic implant produced from the foamable thermoplastic composition). In still other embodiments, the bioactive agent may include, for example: hydroxyapatite, calcium carbonate, bioactive glass, allograft bone components (demineralized bone fibers or matrix), silica nitrite, tricalcium phosphate, and the like. In some aspects, increasing the proportion of bioactive agent in the composition may increase a hardness of the composite, but also increase the brittleness.

In various embodiments, the foamable thermoplastic composition may comprise up to about 80% bioactive agent by weight. In a particular embodiment, the foamable thermoplastic composition may comprise between about 5% and about 80% bioactive agent by weight (e.g., about 70%). In some embodiments, the foamable thermoplastic composition may comprise about 20% bioactive agent by weight. In various aspects, the foamable thermoplastic composition may comprise between about 10% and about 30% bioactive agent by weight.

In particular aspects the chemical foaming agent may include any suitable temperature-sensitive chemical foaming agent configured to change foaming characteristics at different manufacturing temperatures. With increased foaming (e.g., at higher temperatures), the density of a component produced from a plastic comprising the foaming agent may be relatively lower (i.e., decreased). Additionally, the decrease in density at higher foaming may be accompanied by the introduction of micro and/or macro pores in the component. In various embodiments, the chemical foaming agent may include, for example: sodium bicarbonate, citric acid, azodicarbonamide, and/or other suitable compounds with gas-producing decomposition reactions or combinations thereof.

In some aspects, the increase in porosity of the resulting component may further improve the facilitation of bone growth via the presence bioactive agent in the foamable thermoplastic composition. (i.e., because the presence of additional pores in the component may increase a surface area of the implant/component exposed to the surrounding tissue). In some aspects, the foaming agent is selected based on the selected thermoplastic.

In particular aspects, the foamable thermoplastic composition may comprise up to about 10% chemical foaming agent by weight. In various embodiments, the composition of the foamable thermoplastic composition with respect to the chemical foaming agent (or chemical foaming agents) that make up the foamable thermoplastic composition may vary based on the selected chemical foaming agent selected. For example, a particular chemical foaming agent may produce desired foaming at up to 10% of the foamable thermoplastic composition by weight. Another chemical foaming agent may produce the desired foaming at a range of between about 0.5% and 1.5% of the foamable thermoplastic composition by weight. As such, when selecting a chemical foaming agent for use in the foamable thermoplastic composition, the amount of chemical foaming agent used may vary based on one or more of: (1) the selected chemical foaming agent; (2) the desired foaming; (3) the type of implant to be produced; (4) etc.

A method of manufacturing the foamable thermoplastic composition (e.g., a bone growth substrate for use in 3D printing) according to various embodiments include adding a foaming agent and a bioactive agent to a thermoplastic, either one at a time or both together. Any suitable chemical and physical mixing methods may be used prior to melting such that the foaming agent and the bioactive agent are evenly distributed throughout. For example, the thermoplastic may be dissolved with any suitable solvent, and the foaming agent and bioactive agent may be added to the resulting solution, forming a slurry. This slurry may be thoroughly stirred and dried to produce solid composite pellets, which may be used for injection molding. The pellets may alternatively be extruded into a strand of filament for use with a 3D printer. The melting point of the thermoplastic may be lower than the activation temperature of the foaming agent, enabling mixing and extrusion at an intermediate temperature without causing the material to foam. The resulting foamable thermoplastic composition may include a composition in which the biodegradable structural polymer, bioactive agent, and chemical foaming agent are substantially evenly distrusted (e.g., evenly distributed) throughout. The foamable thermoplastic composition may be extruded into a filament for use in 3D printing as described herein.

In a particular embodiment, the foamable thermoplastic composition comprises between about 0.5% and about 1.5% chemical foaming agent by weight. In other embodiments the foamable thermoplastic composition comprises between about 0.5% and 2.5% chemical foaming agent (e.g., citric acid) by weight. In still other embodiments, the foamable thermoplastic composition comprises up to about 4% chemical foaming agent by weight. In yet other embodiments, the foamable thermoplastic composition comprises up to about 15% chemical foaming agent by weight. In some embodiments, the foamable thermoplastic composition comprises between about 15% and about 25% bioactive agent (e.g., hydroxyapatite) by weight.

It should be understood in light of this disclosure that a range describing a percentage by weight of between about 15 percent and about 25 percent is intended to capture and disclose every rational number value percentage between 15 percent and 25 percent (e.g., 15%, 16%, 17%, 18%, 19%, 20%, 21%, 21.1%, 21.01%, 21.001% . . . 24.999%, and so on, including each rational number value between 15 and 25 not listed). In addition, any described range (e.g., describing percentage by weight) is intended to capture and disclose every range within the described range (e.g., between 0.5% and 1.5% is intended to disclosure and capture a range between 0.7% and 1.4% and so on). Additionally, terms such as "about," "substantially," etc., when used to modify structural descriptions or numerical values, are intended to capture the stated shape, value, etc. as well as account for slight variations as a result of, for example, manufacturing tolerances. For example, the term "substantially rectangular" is intended to describe shapes that are both exactly rectangular (e.g., have four sides that meet at ninety degree angles) as well as shapes that are not quite exactly rectangular (e.g., shapes having four sides that meet at an angle in an acceptable tolerance of ninety degrees, such as 90°+/−4°). The term about 20%, for example, is intended to describe and disclosure percentages within a degree of tolerance of the disclosed percentage (e.g., such as 20%+/−4%). Furthermore, although composite compositions are generally described as having a particular component making up a particular percentage of the composition by weight, it should be understood that other embodiments may include those components as the disclosed percentage by volume, mass, or other suitable measure.

As may be understood in light of this disclosure, the material properties of the foamable thermoplastic composition may vary in relation to the temperature at which the foamable thermoplastic composition is 3D printed (i.e., based on the nozzle temperature of the 3D printer) and the properties (e.g., makeup) of the foamable thermoplastic composition. For example, the foamable thermoplastic composition may transition from: (1) a solid composite at a first temperature (e.g., first temperature range) prior to manufacturing; to (2) a melted composite at a temperature above a melting temperature of the plastic (e.g., structural polymer) but below a chemical foaming agent decomposition temperature (e.g., a second temperature range); to (3) a partially foamed composite at a third temperature (e.g., third temperature range); to (4) a fully foamed composite at a fourth temperature (e.g., a fourth temperature range).

Figure 10:
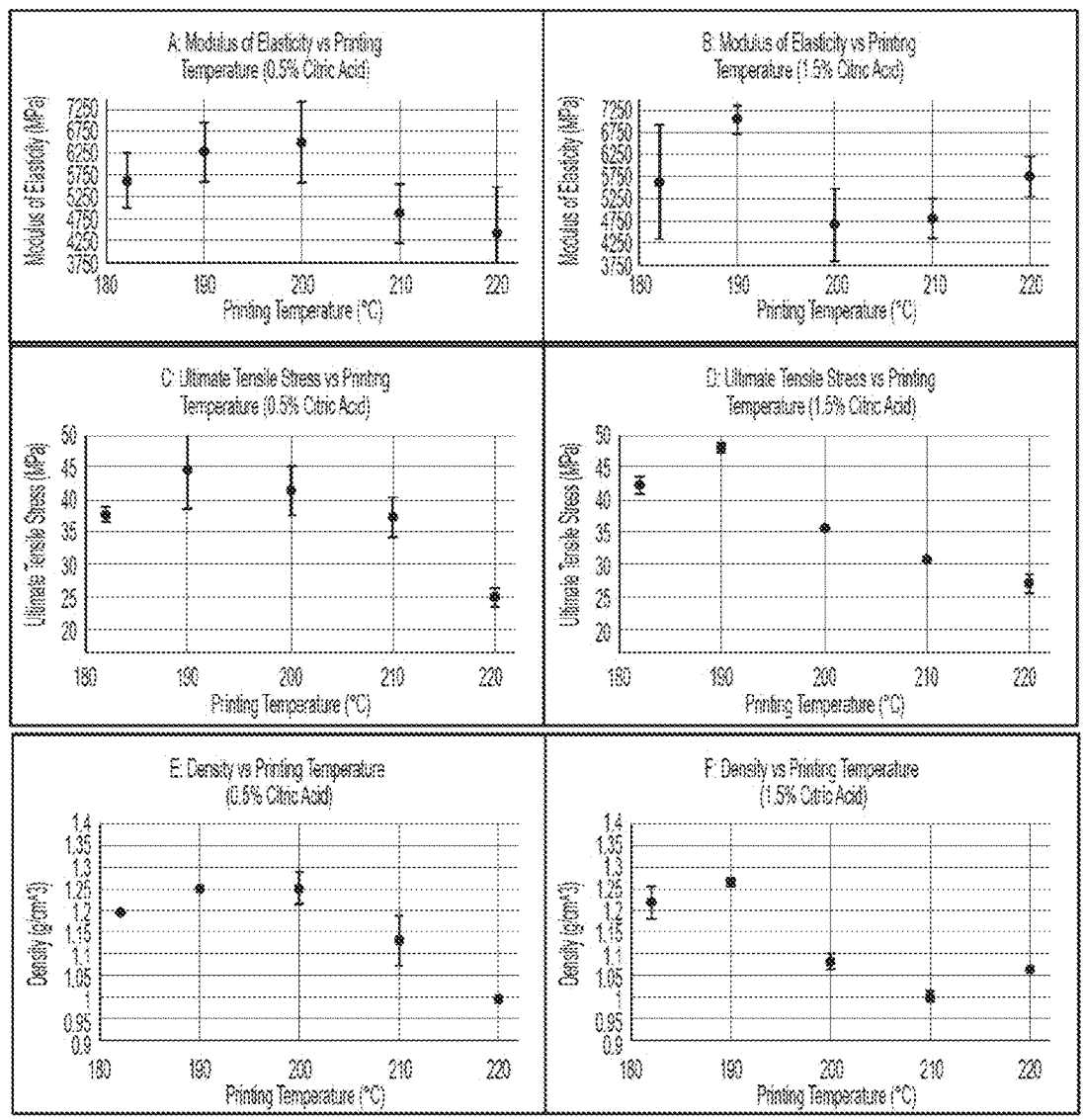
FIG. 10 depicts a set of tables demonstrating the modulus of elasticity, ultimate tensile stress, and average density vs. printing temperature for a foamable thermoplastic composition comprising 0.5% citric acid and 1.5% citric acid by weight respectively.

FIG. 10 depicts modulus of elasticity v. printing temperature, ultimate tensile strength v. printing temperature, and average density v. printing temperature for two filament samples. The two filament samples were prepared at printing temperatures from 182° C. to 220° C. Serial numbers were assigned based on filament type and printing conditions as follows: (1) Filament type: CA 795-200-05:5 [CA (Citric Acid—type of foaming agent) 795 (percentage by weight of PLA—79.5%)-200 (percentage by weight HA—20.0%)-05 (percentage by weight CFA—0.5%):5 (generation of filament sample)]; and CA 795-200-05:5(2) Filament type: CA (Citric Acid—type of foaming agent) 785 (percentage by weight of PLA—78.5%)-200 (percentage by weight HA-20.0%)-15 (percentage by weight CFA—1.5%):5 (generation of filament sample).

As demonstrated in FIG. 10, comparing the 0.5% CFA filament with the 1.5% CFA filament demonstrates a reduction in printing temperature required to change physical properties due to CFA foaming.

In modulus of elasticity, graph A (0.5% by mass CFA) has a peak modulus at 200° C., compared to a peak modulus in graph B (1.5% by mass CFA) at 190° C. The modulus of elasticity is then reduced by 25% in graph A and 33% in graph B.

This relationship between concentrations of CFA is shown in density as well. In graphs E and F, a similar peak was observed at 200° C. for the 0.5% CFA sample and at 190° C. for the 1.5% CFA sample. The density then reduces by 9.7% and 14.8%, respectively.

A similar relationship exists between printing temperature and ultimate tensile stress, as shown in graphs C and D in FIG. 10. While the peak ultimate tensile stress exists for both graphs at 190° C., graph D (1.5% by mass CFA) shows a greater decrease in stress as compared to graph C (0.5% by mass CFA). In graph D, there is a 26.2% reduction in ultimate tensile stress observed. This is much greater than in graph C, where there is a 7.0% decrease in ultimate tensile stress.

Relationships between density and both modulus of elasticity and ultimate tensile stress can be drawn as well. As such, as described herein, in various aspects, the correlation between printing temperature and density, modulus of elasticity, and tensile strength can be leveraged to print a component having a desired property (e.g., density, modulus of elasticity, and tensile strength) at a particular location within the component by adjusting a printing temperature at that particular location.

Using the foamable thermoplastic composition in 3D printing, varying printing temperature in each region of an implant allows an implant to directly reproduce the placement of cortical, trabecular, and other bone and in the patient's original bone. In some aspects, Trabecular bone tissue includes hierarchical, spongy, and porous material composed of hard and soft tissue components which can be found at the epiphyses and metaphyses of long bones and in the vertebral bodies.

In some aspects, cortical bone includes the dense outer surface of bone that forms a protective layer around the internal cavity. This type of bone may make up nearly 80% of skeletal mass and is imperative to body structure and weight bearing because of its high resistance to bending and torsion. In some aspects, adjusting the porosity of 3D printed components may enable a component to more closely mirror the actual structure, properties, and porosity of a patient's bone.

Alternatively, varying temperature when 3D printing the foamable thermoplastic composition can create an entirely new structure having an arrangement, design, and desired properties throughout.

Example Computing Environment

FIG. 1 depicts an example of a computing environment that can be used for producing a patient-specific 3D printed orthopedic implant or other component as described herein. For example, a 3D printing system 100 may be configured to cause a 3D printer 110 to print a component (e.g., patient-specific 3D printed orthopedic implant) according to imaging and density data for the component. As noted above, various aspects may utilize Fused-Deposition-Modeling (FDM) 3D printing (e.g., Fused Filament Fabrication), which can further improve on the limitations of current 3D printing techniques and injection molding solutions for producing implants. FDM 3D printing may require relatively lower cost equipment and enable implant production on-site at hospitals. The 3D printing system 100 may, for example, cause the 3D printer 110 to print the component according to imaging data from a medical imaging scan or other scan of a patient's bone-to-be-printed. The 3D printing system 100 may further cause the 3D printer 110 to print each portion of the component at a particular temperature according to a desired density of each portion of the printed component. In this way, the 3D printing system 100 may be configured to control operation of the 3D printer 110 to produce a component (e.g., patient-specific orthopedic implant) having a desired shape, desired structure, and desired material properties throughout.

FIG. 1 depicts examples of hardware components of a 3D printing system 100 according to various embodiments. In some embodiments, the 3D printing system 100 may include any computing system on which an application for executing actions required as part of the 3D printing process described herein resides. The 3D printing system 100 includes a specialized computing system that may be used for controlling operation of a 3D printer 110.

In some aspects, the 3D printing system 100 may control operation of any suitable 3D printer 110. In some aspects, the 3D printer 110 comprises any suitable stereolithography, selective laser sintering, fused deposition modeling, digital light process, multi jet fusion, polyjet, direct metal laser sintering, electron beam melting, and/or other suitable 3D printer 110. In a particular embodiment, the 3D printer comprises a suitable Fused-Deposition-Modeling (FDM) 3D printer 110. In some aspects, a Fused-Deposition-Modeling (FDM) 3D printer 110 form a component by extruding a filament through a heated nozzle to form the component in a series of layers. In some aspects, the 3D printer 110 comprises at least one heating element and at least one cooling element. In some aspects, the heating and cooling element cooperate to adjust a printing temperature to an instant desired temperature. By including a cooling element, the 3D printer 110 may enable a more instantaneous temperature change such that residual heat from a heated nozzle does not affect or otherwise modify the desired printing temperature. In this way, the 3D printer 110 may produce a component at a faster rate than a 3D printer 110 that does not include a cooling element (e.g., because such a 3D printer may not be configured to alter a printing temperature with sufficient temperature change rate to produce a desired component having desired properties as rapidly based on limitations resulting from temperature change shortcomings).

In some aspects, the one or more cooling elements may include one or more blowers. In other aspects, the one or more cooling elements may include one or more liquid cooling (e.g., water cooling) elements. In some aspects, the one or more cooling elements comprise a pneumatic or other air blast to substantially immediately reduce a temperature of the printing nozzle. In other aspects, the one or more cooling elements comprise any suitable cooling element to substantially instantaneously reduce a temperature of the printing nozzle(s).

In particular embodiments, the 3D printer 110 may include any suitable 3D printer with one or more printing nozzles. For example, any embodiment of the method or process described herein may cause the 3D printer to print and mix multiple different materials by utilizing a different material in each of the nozzles. In various embodiments, the 3D printer 110 is configured to operate each nozzle at a different temperature (e.g., instantaneous temperature during printer. The different temperature may be selected, for example, based on the particular composite or material that is being printed via the respective nozzle. In some aspects, the 3D printer 110 is configured to produce a component (e.g., implant) by utilizing one or more composites that include both biodegradable and non-biodegradable structural polymers. In this way, the process is configured to produce a component (e.g., implant) with at least some non-biodegradable portions. Such implants may be advantageous in cases where a healing rate for a patient following implant may not match a resorption rate of a biodegradable structural polymer.

In some aspects, a remote computing system 130 may provide computing functionality or perform other computing steps with respect to the system and/or process described herein. In some aspects, the remote computing system 130 may communicate with the 3D printing system over a computing network 142.

In particular embodiments, the 3D printing system 100 can include one or more third-party devices such as, for example, one or more servers operating in a distributed manner. The 3D printing system 100 can include any computing device or group of computing devices, and/or one or more server devices. The user interface configuration and presentation system 100 may include computing hardware performing different processes for described herein with relation to causing a 3D printer to form a component using image, temperature, and other data. For instance, the user 3D printing system 100 executes a component printing module 200 to cause a 3D printer to print a component.

In other embodiments, the 3D printing system 100 includes one or more data repositories 120 that may include, for example, store data related to the 3D printing functions described herein. In various embodiments, the one or more configurable blocks 125 include stored content blocks which a user may, for example request to include in a generated user interface. In some embodiments, the stored content blocks 125 include one or more pieces of content and a defined presentation time (e.g., length).

The number of devices depicted in FIG. 1 are provided for illustrative purposes. It should be understood that, in some embodiments, different number of devices may be used. In various embodiments, for example, while certain devices or systems are shown as single devices in FIG. 1, multiple devices may instead be used to implement these devices or systems.

Component Printing Module and Associated Process

Figure 2:
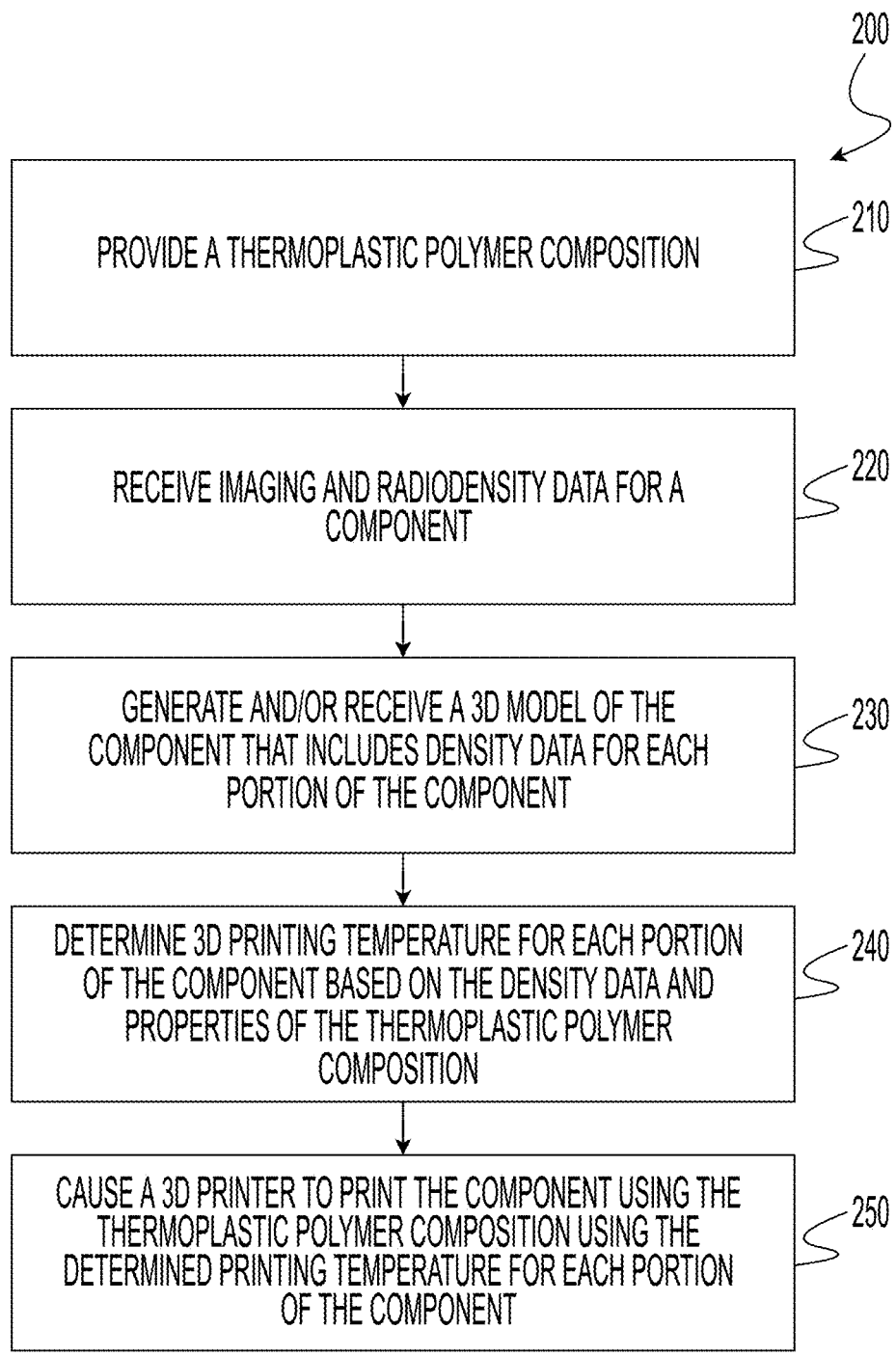
FIG. 2 depicts an example of a process for producing a 3D printed component.

FIG. 2 depicts an example of a component printing module 200 (e.g., process), including a process for producing a 3D printed component, such as a bone implant. This process includes method steps in addition to operations that the 3D printing system 100 may execute to cause a 3D printer to produce a three dimensional component having desired physical properties. For instance, the flow diagram shown in FIG. 2 may correspond to operations carried out, for example, by computing hardware found in the 3D printing system 100, as the computing hardware executes the user interface configuration module 200 as well as method steps performed by an entity (e.g., individual, corporation, etc.) in order to produce a patient-specific orthopedic implant or other component. The flow diagram further includes process steps that may, for example, be carried out as part of the 3D printing method described herein.

In particular embodiments, the process shown in FIG. 2 begins, at Step 210, with providing a thermoplastic polymer composition. In various aspects, the thermoplastic polymer composition may be utilized as part of the process for 3D printing a particular component, such as a bone implant. In various embodiments, the thermoplastic polymer composition comprises material suitable for manufacturing a component such as a bone growth substrate. In any embodiment described herein, the thermoplastic polymer composition may comprise any suitable polymer described herein. In particular embodiments, the thermoplastic polymer composition comprises a foamable thermoplastic composition comprising: (1) a structural polymer (e.g., biodegradable and/or non-biodegradable structural polymer); (2) a bioactive agent; and (3) a chemical foaming agent. In particular embodiments, the foamable thermoplastic composition is configured for forming a 3D printed component (e.g., bone implant) having a density in each portion of the 3D printed component that corresponds to a temperature at which that portion of the 3D printed component was 3D printed. In some aspects, the foamable thermoplastic composition includes any suitable heat activated foaming agent operative to manufacture a bone growth substrate with a textured surface having pores on a macro level, a micro level, and a nanoparticle level to facilitate rapid bone growth. In particular aspects, the thermoplastic polymer composition comprises any suitable composition described herein.

Turning to Step 220, the process involves receiving imaging and radiodensity data for a component (e.g., an orthopedic implant). In particular aspects, the step of receiving the imaging and radiodensity data may be carried out by computing hardware found in the 3D printing system 100, as the 3D printing system 100 executes a component printing module 200. When executing the component printing module 200, the 3D printing system 100 may receive the imaging and radiodensity data from a remote computing device 130, such as a remote computing device 130 involved in taking or otherwise processing the imaging and/or radiodensity data. For example, the 3D printing system 100 may receive the imaging and/or radiodensity data from any suitable medical imaging device (e.g., via a Computed Tomography [CT] scan). In various aspects, the imaging data may include a three dimensional image or model of a patient's bone (e.g., or portion thereof). In particular embodiments, the three dimensional image may include at least a portion of a patient's bone or other component that is to be 3D printed as part of the process described herein. In particular embodiments, the 3D model may include location-specific radiodensity data throughout the model of the component. In this way, the imaging and radiodensity data may provide structural and material property data (e.g., density, tensile strength, modulus of elasticity) for each portion of the component to be 3D printed.

In some aspects, the process may involve taking one or more images and or radiodensity analysis of a component. For example, the process may involve taking one or more medical images (e.g., via a CT scan, bone density scan, MRI or other scan) of a patient's bone that needs to be reproduced. The imaging and radiodensity data may provide patient-specific bone-structure and density throughout of the implant to be produced. In this way, the system and process may acquire (e.g., actively by performing the imaging or by receiving the data from a separate system or source) patient-specific bone data in order to produce a patient-specific implant that has a structure and properties that mirror the patient's actual bone.

Continuing to Step 230, the system generates and/or receives a 3D model of the component that includes density data for each portion of the component. In some aspects, the system generates the 3D model from the imaging data received at Step 220 (e.g., the 3D model is based on the imaging and radiodensity data). In some embodiments, the radiodensity data may include a value on the Hounsfield scale that corresponds to each portion of the 3D model. In some embodiments, the system receives the 3D model (including density data) that has been generated by a separate computing system (e.g., the remote computing device 130).

At Step 240, the system determines a 3D printing temperature for each portion of the component based on the density data and properties of the thermoplastic polymer composition. In various embodiments, a desired density (e.g., or other material property) of each portion of a component has a corresponding 3D printing temperature. In various aspects, the system is configured to determine a corresponding temperature for the density of each component (e.g., defined by the radiodensity data). In other embodiments, the system receives temperature data for a particular 3D printed component from a remote computing system 130 (e.g., a remote computing entity that determines corresponding temperature data for a particular component production).

In some aspects, the 3D printing temperature is further based on material makeup of the thermoplastic polymer composition. For example, as may be understood in light of this disclosure, different makeups of composites may have different corresponding temperatures to achieve desired material properties. As such, a particular component being produced from a particular composite may require particular printing temperature for each portion of the component. Accordingly, each printing temperature of each portion of each layer of each 3D printed component may have a unique printing temperature defined by both the desired material property and the composite used in the 3D printing.

At Step 250, the system causes a 3D printer 110 to print the component using the thermoplastic polymer composition at the determined printing temperature for each portion of the component. For example, as may be understood in light of this disclosure, when 3D printing with the thermoplastic polymer composition (e.g., foamable thermoplastic composition), the 3D printing system 100 may be configured to modify the instant printing temperature as the 3D printer 110 printer prints each portion of each layer of the component (e.g., orthopedic implant). In this way, the 3D printing system 100 may be configured to manufacture a patient-specific component (e.g., implant) having a 3D structure defined by the imaging data having material properties (e.g., density, modulus of elasticity, etc.) at each particular location within the component that corresponds to a desired material property (e.g., defined by the radiodensity).

The 3D printing system 100 may cause the 3D printer 110 to print each portion of the component at a particular temperature according to a desired density (or other desired material property) of each portion of the printed component. In this way, the 3D printing system 100 may be configured to control operation of the 3D printer 110 to produce a component (e.g., patient-specific orthopedic implant) having a desired shape, desired structure, and desired material properties throughout. In some aspects, the 3D printing temperature is further based on material makeup of the thermoplastic polymer composition. For example, as may be understood in light of this disclosure, different makeups of composites may have different corresponding temperatures to achieve desired material properties. As such, a particular component being produced from a particular composite may require particular printing temperature for each portion of the component. Accordingly, each printing temperature of each portion of each layer of each 3D printed component may have a unique printing temperature defined by both the desired material property and the composite used in the 3D printing.

Figure 3:
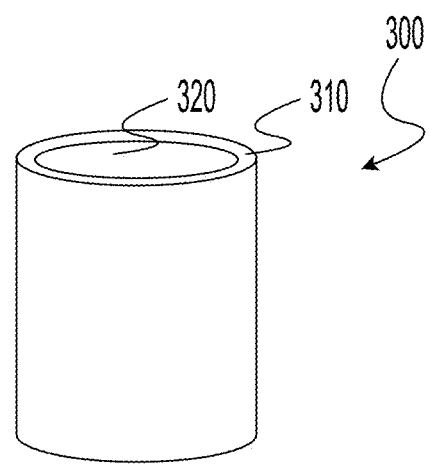
FIG. 3 depicts an example of a cross section of 3D printed component having varying density.

FIG. 3 depicts an example of a cross section of a 3D printed component 300 having varying density. As may be understood from this figure, the 3D printed component comprises an outer portion 310 and an inner portion 320. In some aspects, the outer portion 310 has a different density than the inner portion 320. As may be understood from this disclosure, when 3D printing this component 300, the 3D printer may print each layer of the outer portion 310 at a first temperature (e.g., that corresponds to the first density) and print each layer of the inner portion 320 at a second temperature (e.g., that corresponds to the second density). In some embodiments, the first density is different than the second density. In particular embodiments, at least one of the first or second densities is above and/or below the foaming temperature of the chemical foaming agent that makes up at least a portion of the thermoplastic polymer composition.

Figure 4:
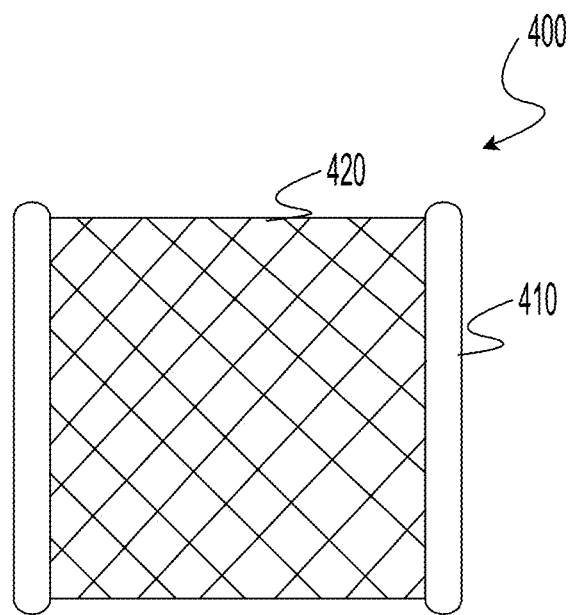
FIG. 4 depicts another example of a cross section of 3D printed component having varying density.

FIG. 4 depicts an example of a cross sectional slice of a 3D printed component 400 having varying density. As may be understood from this figure, the 3D printed component 400 comprises a first density portion 410 and a second density portion 420. In some aspects, the first density portion 410 has a different density than the second density portion 420. As may be understood from this disclosure, when 3D printing this component 4, the 3D printer may print each portion of the first density portion 410 at a first temperature (e.g., that corresponds to the first density) and print each layer of the second density portion 420 at a second temperature (e.g., that corresponds to the second density). In some embodiments, the first density is different than the second density. In particular embodiments, at least one of the first or second densities is above and/or below the foaming temperature of the chemical foaming agent that makes up at least a portion of the thermoplastic polymer composition. In some aspects, the component portion 400 shown in FIG. 4 represents a single 3D printed layer of a component. As may be understood from this figure, various embodiments of a patient-specific component (e.g., implant) may include an internal lattice structure having the first density (e.g., the first density portion 410). In some embodiments, this first density portion 410 in the form of the lattice may provide structural support to the overall component 400. In this way, in various aspects, a particular component (e.g., implant) may be designed specifically for the structural and material needs of a patient's implant.

Example Technical Platforms

Aspects of the present disclosure may be implemented in various ways, including as computer program products that include articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query, or search language, and/or a report writing language. In one or more example aspects, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established, or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

According to various aspects, a non-volatile computer-readable storage medium may include a floppy disk, flexible disk, hard disk, solid-state storage (SSS) (e.g., a solid-state drive (SSD), solid state card (SSC), solid state module (SSM)), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

According to various aspects, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where various aspects are described to use a computer-readable storage medium, other types of computer-readable storage media may be substituted for or used in addition to the computer-readable storage media described above.

Various aspects of the present disclosure may also be implemented as methods, apparatuses, systems, computing devices, computing entities, and/or the like. As such, various aspects of the present disclosure may take the form of a data structure, apparatus, system, computing device, computing entity, and/or the like executing instructions stored on a computer-readable storage medium to perform certain steps or operations. Thus, various aspects of the present disclosure also may take the form of entirely hardware, entirely computer program product, and/or a combination of computer program product and hardware performing certain steps or operations.

Various aspects of the present disclosure are described herein with reference to block diagrams and flowchart illustrations. Thus, each block of the block diagrams and flowchart illustrations may be implemented in the form of a computer program product, an entirely hardware aspect, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some examples of aspects, retrieval, loading, and/or execution may be performed in parallel such that multiple instructions are retrieved, loaded, and/or executed together. Thus, such aspects can produce specially configured machines performing the steps or operations specified in the block diagrams and flowchart illustrations. Accordingly, the block diagrams and flowchart illustrations support various combinations of aspects for performing the specified instructions, operations, or steps.

Example System Architecture

Figure 5:
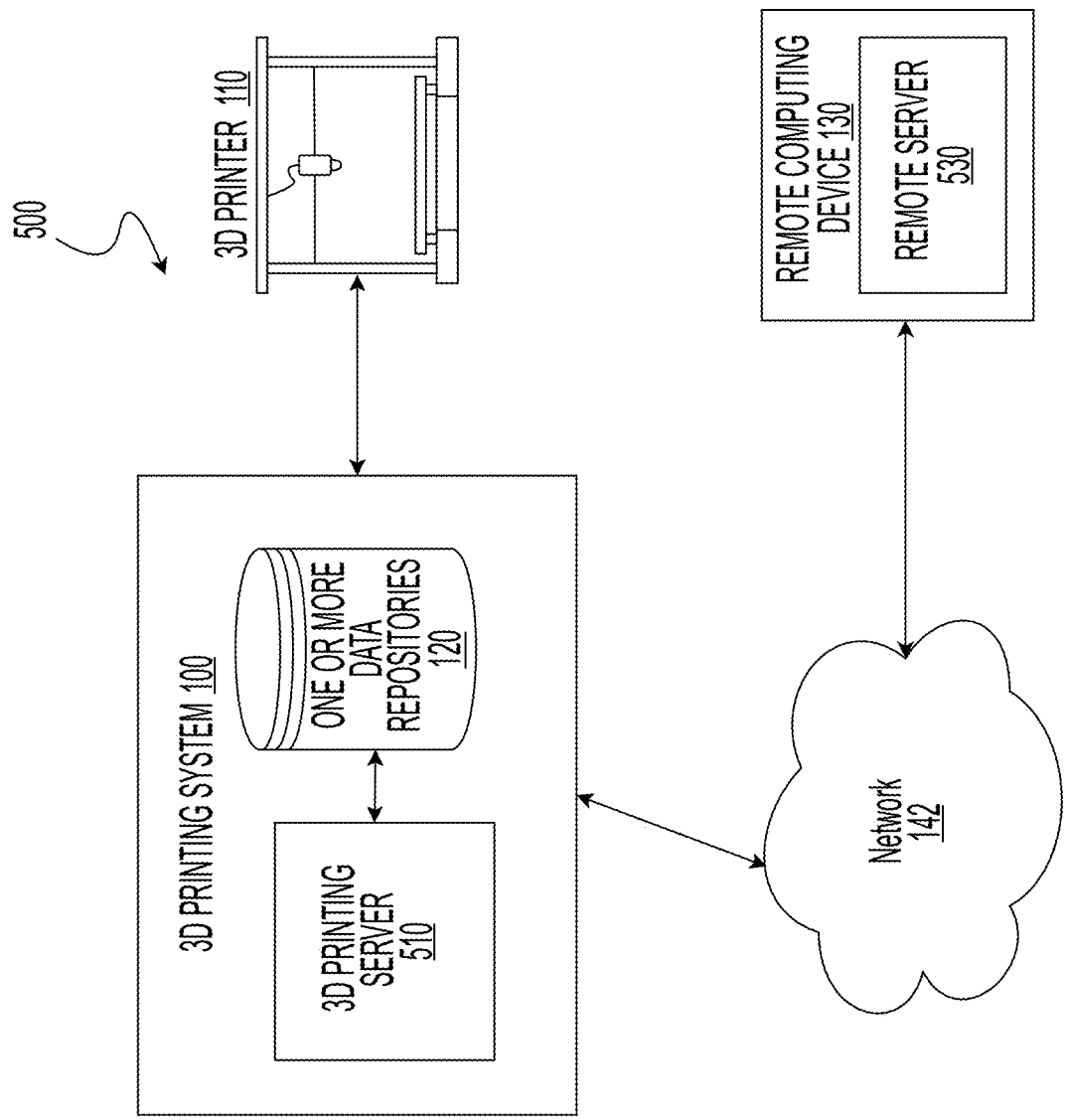
FIG. 5 depicts an example of a system architecture that may be used in accordance with various aspects of the present disclosure.

FIG. 5 an example of a computing environment that can be used for generating a 3D printed component (e.g., such as a bone implant) in accordance with various embodiments of the present disclosure. Components of the system architecture 500 are configured according to various aspects to configure software on remove computing devices on a private computing system 100.

As may be understood from FIG. 5, the system architecture 500 according to various aspects may include a 3D printing system 100 that includes a 3D printing server 510 and one or more data repositories 120. Although the 3D printing server 510, 3D printing system 100, and one or more data repositories 120 are shown as separate components, according to other aspects, these components may include a single server and/or repository, servers and/or repositories, one or more cloud-based servers and/or repositories, or any other suitable configuration.

In addition, the system architecture 500 according to various aspects may include a remote computing device (e.g., remote computing system) 130 that includes one or more remote servers 530. Although the one or more remote servers 530 and remote computing system (e.g., device) 130 are shown as separate components, according to other aspects, these components may include a single server and/or repository, servers and/or repositories, one or more cloud-based servers and/or repositories, or any other suitable configuration.

The one or more remote servers 530, 3D printing server 510, and/or other components may communicate with, access, and/or the like with each other over one or more networks, such as via a public data network public data network 142 and/or a private data network private data network 142, or other network 142. Furthermore, one or more remote servers 530 and/or 3D printing server 510, may provide one or more interfaces that allow the 3D printing system 100, the remote computing device 130, etc. to communicate with each other such as one or more suitable application programming interfaces (APIs), direct connections, and/or the like.

Example Computing Hardware

Figure 6:
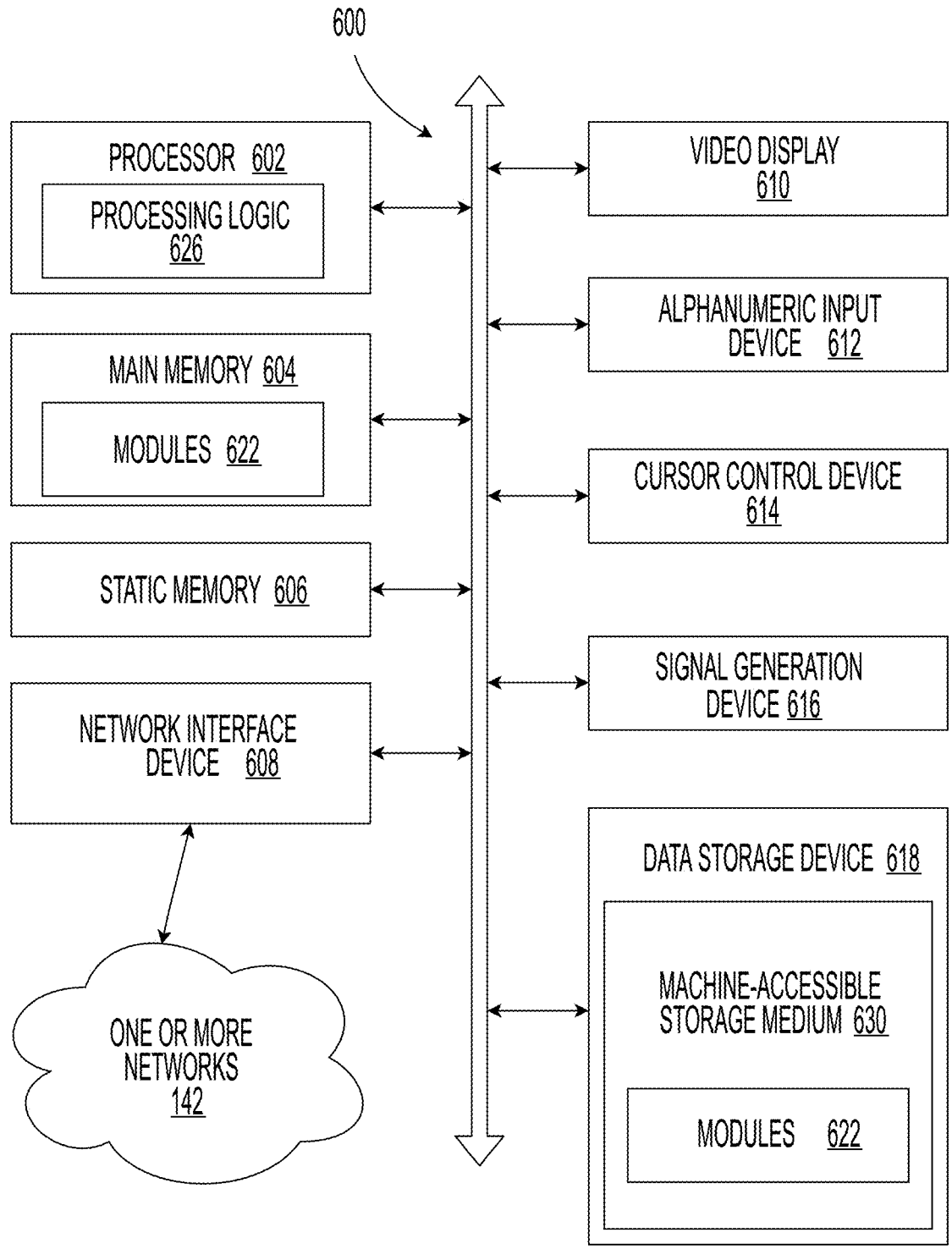
FIG. 6 depicts an example of a computing entity that may be used in accordance with various embodiments of the present disclosure.

FIG. 6 illustrates a diagrammatic representation of a computing hardware device 600 that may be used in accordance with various aspects of the disclosure. For example, the hardware device 600 may be computing hardware such as a remote server 540 or a device management server 504 shown in FIG. 5. According to particular aspects, the hardware device 600 may be connected (e.g., networked) to one or more other computing entities, storage devices, and/or the like via one or more networks such as, for example, a LAN, an intranet, an extranet, and/or the Internet. As noted above, the hardware device 600 may operate in the capacity of a server and/or a client device in a client-server network environment, or as a peer computing device in a peer-to-peer (or distributed) network environment. According to various aspects, the hardware device 800 may be a personal computer (PC), a tablet PC, a set-top box (STB), a Personal Digital Assistant (PDA), a mobile device (smartphone), a web appliance, a server, a network router, a switch or bridge, or any other device capable of executing a set of instructions (sequential or otherwise) that specify actions to be taken by that device. Further, while only a single hardware device 600 is illustrated, the term "hardware device," "computing hardware," and/or the like shall also be taken to include any collection of computing entities that individually or jointly execute a set (or multiple sets) of instructions to perform any one or more of the methodologies discussed herein.

A hardware device 600 includes a processor 602, a main memory 604 (e.g., read-only memory (ROM), flash memory, dynamic random-access memory (DRAM) such as synchronous DRAM (SDRAM), Rambus DRAM (RDRAM), and/or the like), a static memory 606 (e.g., flash memory, static random-access memory (SRAM), and/or the like), and a data storage device 618, that communicate with each other via a bus 632.

The processor 602 may represent one or more general-purpose processing devices such as a microprocessor, a central processing unit, and/or the like. According to some aspects, the processor 602 may be a complex instruction set computing (CISC) microprocessor, reduced instruction set computing (RISC) microprocessor, very long instruction word (VLIW) microprocessor, a processor implementing other instruction sets, processors implementing a combination of instruction sets, and/or the like. According to some aspects, the processor 602 may be one or more special-purpose processing devices such as an application specific integrated circuit (ASIC), a field programmable gate array (FPGA), a digital signal processor (DSP), network processor, and/or the like. The processor 602 can execute processing logic 626 for performing various operations and/or steps described herein.

The hardware device 600 may further include a network interface device 608, as well as a video display unit 610 (e.g., a liquid crystal display (LCD), a cathode ray tube (CRT), and/or the like), an alphanumeric input device 612 (e.g., a keyboard), a cursor control device 614 (e.g., a mouse, a trackpad), and/or a signal generation device 616 (e.g., a speaker). The hardware device 600 may further include a data storage device 618. The data storage device 618 may include a non-transitory computer-readable storage medium 630 (also known as a non-transitory computer-readable storage medium or a non-transitory computer-readable medium) on which is stored one or more modules 622 (e.g., sets of software instructions) embodying any one or more of the methodologies or functions described herein. For instance, according to particular aspects, the modules 622 include the networked computing device registration module 200, the remote software installation module 300, and/or the remote software configuration module 400 as described herein. The one or more modules 622 may also reside, completely or at least partially, within main memory 604 and/or within the processor 602 during execution thereof by the hardware device 600—main memory 604 and processor 602 also constituting computer-accessible storage media. The one or more modules 622 may further be transmitted or received over a private data network 144 and/or a public data network 142 via the network interface device 608.

While the computer-readable storage medium 630 is shown to be a single medium, the terms "computer-readable storage medium" and "machine-accessible storage medium" should be understood to include a single medium or multiple media (e.g., a centralized or distributed database, and/or associated caches and servers) that store the one or more sets of instructions. The term "computer-readable storage medium" should also be understood to include any medium that is capable of storing, encoding, and/or carrying a set of instructions for execution by the hardware device 600 and that causes the hardware device 600 to perform any one or more of the methodologies of the present disclosure. The term "computer-readable storage medium" should accordingly be understood to include, but not be limited to, solid-state memories, optical and magnetic media, and/or the like.

System Operation

The logical operations described herein may be implemented (1) as a sequence of computer implemented acts or one or more program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, steps, structural devices, acts, or modules. These states, operations, steps, structural devices, acts, and modules may be implemented in software, in firmware, in special purpose digital logic, and any combination thereof. Greater or fewer operations may be performed than shown in the figures and described herein. These operations also may be performed in a different order than those described herein.

Exemplary Composite and/or Substrate

Figure 7:
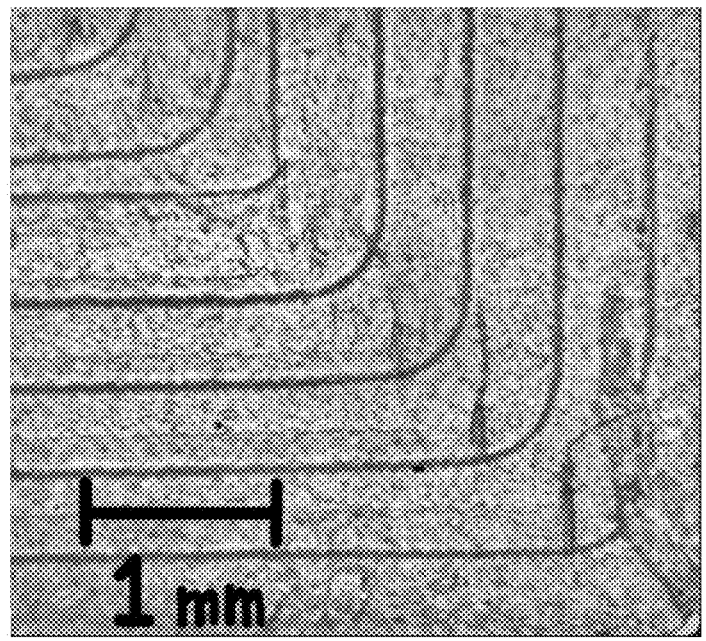
FIG. 7 depicts an example of a 3D printed composite in accordance with various embodiments of the present disclosure.
Figure 8:
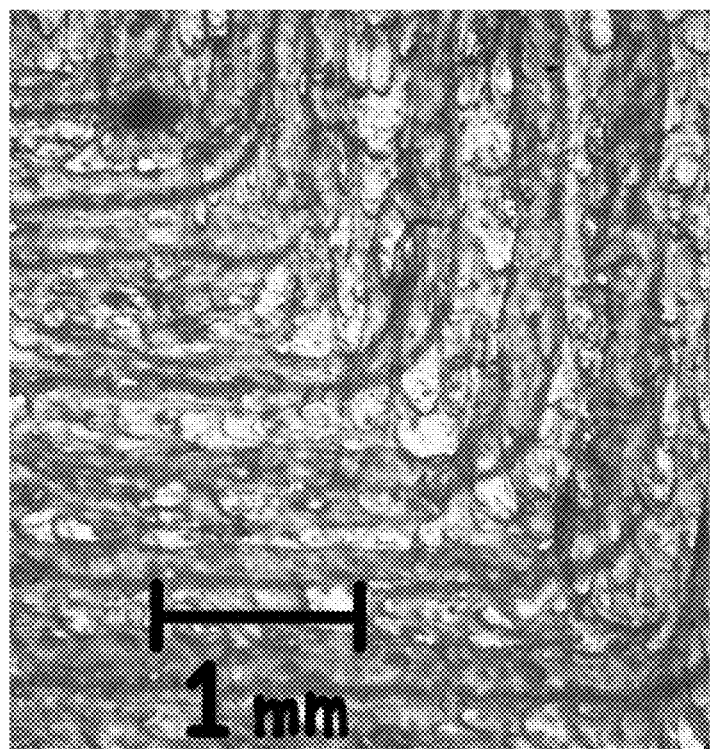
FIG. 8 depicts another example of a 3D printed composite in accordance with various embodiments of the present disclosure.

FIGS. 7 and 8 depicts an illustrative example of a 3D printed layer of the foamable thermoplastic composition printed at different temperatures. In the example shown in FIG. 7, the layer is about 0.2 mm thick and comprises 1.5% chemical foaming agent by weight. FIG. 7 depicts a layer printed at 182 degrees Celsius (e.g., below the foaming temperature of the composite) and FIG. 8 depicts a layer printed at 220 degrees Celsius (e.g., above the foaming temperature of the composite). As may be understood from these figures, the foaming action depicted in FIG. 8 has the effect of changing the surface structure of the printed composite. Such a structure may, for example, provide a surface structure similar to trabecular bone.

Figure 9:
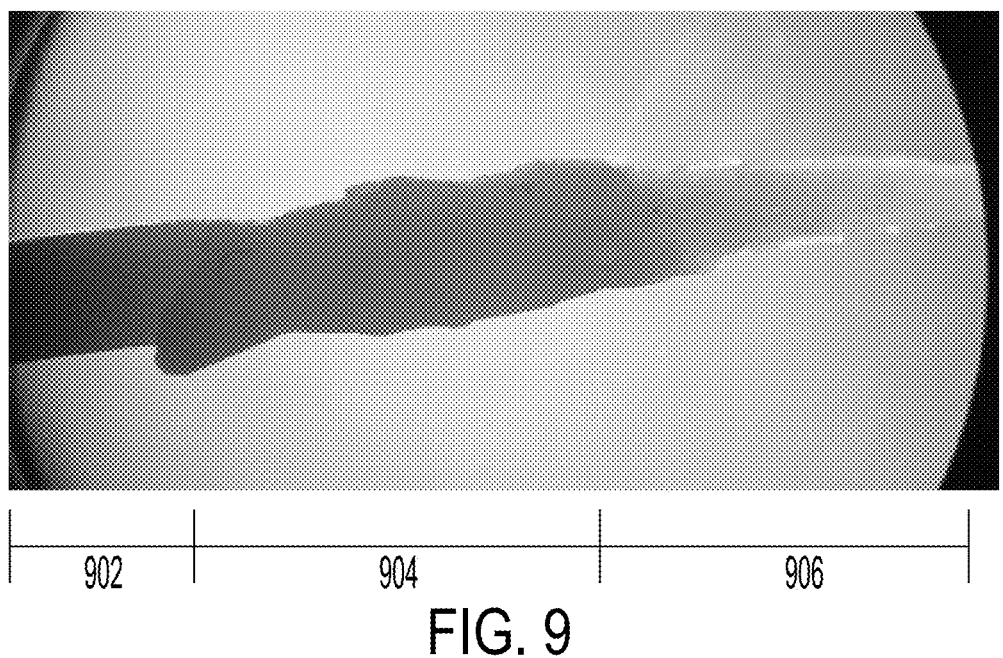
FIG. 9 depicts a partially-foamed composite filament according to various embodiments of the present disclosure.

FIG. 9 depicts an illustrative example of a partially foamed composite filament. As may be understood from this illustrative image, the partially foamed composite filament comprises: (1) a first portion 902 that is a solid filament pre-extrusion; (2) a second portion 904 that is a melted composite under the foaming temperature; and (3) a third portion 906 showing the melted composite above the foaming temperature. As may be understood from this figure and this disclosure, adjusting the printing temperature of the composite (e.g., relative to the foaming temperature) clearly results in a finished component having different material properties throughout.

CONCLUSION

Many modifications and other embodiments of the invention will come to mind to one skilled in the art to which this invention pertains having the benefit of the teachings presented in the foregoing descriptions and the associated drawings. While this specification contains many specific embodiment details, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, while some steps may be described as occurring in response to (e.g., or at least partially in response to) particular other steps, it should be understood that, in other embodiments, such steps may occur independent of (e.g., or coincident with) one another. In certain circumstances, multitasking and parallel processing may be advantageous. Moreover, the separation of various system components in the embodiments described above should not be understood as requiring such separation in all embodiments, and it should be understood that the described program components and systems may be generally integrated together in a single software product or packaged into multiple software products.

In addition, it should be understood that various embodiments may omit any of the steps described above or add additional steps. Furthermore, any numerical ranges described herein are intended to capture every integer and fractional value within the described range (e.g., every rational number value within the described range).

For example, it should be understood that a range describing a percentage by weight of between about 10 percent and about 30 percent is intended to capture and disclose every rational number value percentage between 10 percent and 30 percent (e.g., 11%, 12%, 13%, 14%, 15%, 16%, 17%, 18%, 19%, 20%, 21%, 21.1%, 21.01%, 21.001% . . . 21.999%, 22%, 23%, 24%, 25%, 26%, 27%, 28%, 29%, 30%, and so on). In addition, any described range (e.g., describing percentage by weight) is intended to capture and disclose every range within the described range (e.g., between 0.5% and 1.5% is intended to disclosure and capture a range between 0.7% and 1.4% and so on). Additionally, terms such as "about," "substantially," etc., when used to modify structural descriptions or numerical values, are intended to capture the stated shape, value, etc. as well as account for slight variations as a result of, for example, manufacturing tolerances. For example, the term "substantially rectangular" is intended to describe shapes that are both exactly rectangular (e.g., have four sides that meet at ninety degree angles) as well as shapes that are not quite exactly rectangular (e.g., shapes having four sides that meet at an angle in an acceptable tolerance of ninety degrees, such as 90°+/−4°). The term about 20%, for example, is intended to describe and disclosure percentages within a degree of tolerance of the disclosed percentage (e.g., such as 20%+/−4%).

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A method for 3D printing a patient-specific bone implant having variable density, the method comprising:
   providing a thermoplastic polymer composition comprising:
      between about 20% and about 50% bioactive agent by weight;
      between about 0.5% and about 10% chemical foaming agent by weight; and
      balance structural polymer by weight;
   receiving, by computing hardware, a scan of a bone, the scan comprising at least a 3D image of the bone and radiodensity data for the bone; and
   causing, by the computing hardware, a 3D printer to form the patient-specific bone implant from the 3D image using the thermoplastic polymer by modifying a 3D printing temperature of the 3D printer during printing of the patient-specific bone implant such that each portion of the patient-specific bone implant is produced at a temperature that corresponds to a desired density defined by the radiodensity data for the bone by adjusting a nozzle temperature of the 3D printer while the 3D printer is forming the patient-specific bone implant.

2. The method of claim 1, wherein the structural polymer comprises at least one of: (1) poly(lactic-acid); (2) poly(L-lactic acid); (3) poly(D-lactic acid); (4) poly(D-L-lactic acid); (5) poly-ether-ether-keytone; (6) poly-methyl methacrylate; or (7) poly(lactic-co-glycolic acid).

3. The method of claim 2, wherein the structural polymer comprises polylactic-acid (PLA).

4. The method of claim 1, wherein the bioactive agent comprises at least one of hydroxyapatite, calcium carbonate, bioactive glass, allograft bone components, silica nitrite, or tricalcium phosphate.

5. The method of claim 1, wherein the chemical foaming comprises citric acid.

6. The method of claim 1, wherein:
   the 3D printer comprises a heating element and a cooling element; and
   causing the 3D printer to form the patient-specific bone implant from the 3D image using the thermoplastic polymer by modifying the printing temperature of the 3D printer during printing such that each portion of the patient-specific bone implant is produced at the temperature that corresponds to the desired density defined by the radiodensity data for the bone comprises causing each of the cooling element and the heating element to cooperate to heat the thermoplastic polymer composition to the temperature that corresponds to the desired density defined by the radiodensity data during 3D printing of each portion of the patient-specific bone implant.

7. The method of claim 1, further comprising:
   determining, by the computing hardware, a 3D printing temperature for each portion of the patient-specific bone implant based on the radiodensity data and one or more properties of the thermoplastic polymer composition.

8. A method for producing a variable density 3D printed component, the method comprising:
   providing a thermoplastic polymer composition comprising:
      between about 20% and about 50% bioactive agent by weight;
      between about 0% and about 10% chemical foaming agent by weight; and
      between about 40% and about 80% thermoplastic by weight; and
   causing, by computing hardware, a 3D printer to form the variable density 3D printed component from a 3D model using the thermoplastic polymer composition by adjusting a 3D printing temperature of the 3D printer during printing of the variable density 3D printed component such that each portion of the variable density 3D printed component is produced at a temperature that corresponds to a desired density of each portion of the variable density 3D printed component by adjusting a nozzle temperature of the 3D printer while the 3D printer is forming the variable density 3D printed component.

9. The method of claim 8, wherein the thermoplastic comprises at least one of: (1) poly(lactic-acid); (2) poly(L-lactic acid); (3) poly(D-lactic acid); (4) poly(D-L-lactic acid); (5) poly-ether-ether-keytone; (6) poly-methyl methacrylate; or (7) poly(lactic-co-glycolic acid).

10. The method of claim 9, wherein the thermoplastic comprises polylactic-acid (PLA).

11. The method of claim 8, wherein the bioactive agent comprises hydroxyapatite.

12. The method of claim 8, wherein the chemical foaming comprises sodium bicarbonate, citric acid, or azodicarbonamide.

13. The method of claim 8, wherein:
   the 3D printer comprises a heating element and a cooling element; and causing the 3D printer to form the variable density 3D printed component comprises causing each of the cooling element and the heating element to cooperate to heat the thermoplastic polymer composition to the temperature that corresponds to the desired density.

14. The method of claim 8, further comprising:
determining, by the computing hardware, the 3D printing temperature for each portion of the 3D printed component based on radiodensity data for the 3D printed component and one or more properties of the thermoplastic polymer composition.

15. The method of claim 8, further comprising using imaging data and radiodensity data for a desired component to determine the 3D printing temperature for each portion of the 3D printed component.

16. The method of claim 15, the method further comprising selecting the thermoplastic polymer composition such that the portion of bioactive agent, chemical foaming agent, and thermoplastic produces the desired density at the 3D printing temperature that corresponds to the desired density.

17. The method of claim 15, wherein the imaging data for the desired component comprises data derived from a CT scan.

18. The method of claim 17, wherein:
the desired component comprises a patient's bone; and
the 3D printed component comprises a patient-specific bone implant that corresponds to the patient's bone.

19. The method of claim 8, wherein causing the 3D printer to form the variable density 3D printed component comprises causing the 3D printer to print each layer of the 3D printed component such that each portion of each layer is printed at a temperature that corresponds to the desired density.

20. The method of claim 19, further comprising determining the temperature that corresponds to the desired density of each portion of the variable density 3D printed component based on radiodensity data for the 3D printed component and one or more properties of the thermoplastic polymer.

* * * * *